United States Patent [19]

Geering

[11] 4,275,060

[45] Jun. 23, 1981

[54] METHOD AND COMPOSITION FOR COMBATTING PEST

[75] Inventor: Quinton A. Geering, Little Eversden, England

[73] Assignee: Fisons Limited, London, England

[21] Appl. No.: 58,811

[22] Filed: Jul. 17, 1979

[30] Foreign Application Priority Data

Jul. 19, 1978 [GB] United Kingdom ............... 30420/78
Oct. 17, 1978 [GB] United Kingdom ............... 40882/78
Nov. 23, 1978 [GB] United Kingdom ............... 45861/78

[51] Int. Cl.$^3$ ..................... A01N 57/00; A01N 43/16; A01N 37/00; A01N 37/34
[52] U.S. Cl. .................... 424/218; 424/282; 424/285; 424/304; 424/306
[58] Field of Search ............................... 424/218, 282

[56] References Cited

U.S. PATENT DOCUMENTS

3,962,415  6/1976  Hennart et al. ...................... 424/282

FOREIGN PATENT DOCUMENTS

2260947 10/1975 France ..................................... 424/218

OTHER PUBLICATIONS

The Merck Index, 9th ed. (1976), items 1041 and 5973.
Chem. Abst. 83, 159,092(s), (1975), Wolfenberger et al.

*Primary Examiner*—Douglas W. Robinson
*Attorney, Agent, or Firm*—Wenderoth, Lind & Ponack

[57] ABSTRACT

Combinations of (A) bendiocarb and (B) at least one of methyl parathion and a synthetic pyrethroid combat pests such as Insecta eggs.

7 Claims, No Drawings

METHOD AND COMPOSITION FOR COMBATTING PEST

This invention relates to methods and compositions for combating pests, particularly Insecta eggs.

Accordingly, the invention provides a method of combating Insecta eggs at a locus infested or liable to be infested with them, which method comprises applying to the locus an Insecta egg combating amount of:
(A) bendiocarb; and
(B) at least one pesticide selected from methyl parathion and a synthetic pyrethroid.

The invention also provides an Insecta ovicidal composition comprising (A) and (B).

Bendiocarb is 2,2-dimethyl-1,3-benzodioxol-4-yl methylcarbamate. Methyl parathion is 0,0-dimethyl 0-4-nitrophenyl phosphorothioate.

The present combination of (A) and (B) is surprisingly advantageous. It produces an unexpectedly good combination of high activity against Insecta eggs and safety to crops.

(B) is preferably methyl parathion or a synthetic pyrethroid, though a combination of both can be employed.

When a synthetic pyrethroid is employed, preferably a single one is used though more than one can be used.

The synthetic pyrethroid can be for example
(a) α-cyano-3-phenoxybenzyl 3-(2,2-dibromovinyl)-2,2-dimethylcyclopropanecarboxylate,
(b) α-cyano-3-phenoxybenzyl 3-(2,2-dichlorovinyl)-2,2-dimethylcyclopropanecarboxylate,
(c) 3-phenoxybenzyl 3-(2,2-dichlorovinyl)-2,2-dimethylcyclopropanecarboxylate,
(d) 5-benzyl-3-furylmethyl 3-(2,2-dichlorovinyl)-2,2-dimethylcyclopropanecarboxylate, or
(e) α-cyano-3-phenoxybenzyl 2-(4-chlorophenyl)-3-methylbutyrate.

It is especially preferred that the synthetic pyrethroid comprise (e), fenvalerate.

The synthetic pyrethroid may be in the form of any of the isomers. Mixtures of the isomers are often produced in practice and these mixtures may be employed. Preferably (a) is the 1R-[1α(S*),3α] isomer or a mixture of isomers, (c) is the trans-(±) isomer, the 1R-trans isomer, the cis-(±) isomer or the 1R-cis isomer or a mixture of isomers, and (d) is the trans-(±) isomer, the 1R-trans isomer, the cis-(±) isomer or the 1R-cis isomer or a mixture of isomers.

For instance, (B) can be one or more of the 1R-[1α(S*),3α] isomer of (a), a mixture of isomers of (a), the 1R-trans isomer of (c), the 1R-cis isomer of (c) or a mixture of isomers of (c). In a preferred embodiment, (B) is permethrin, 3-phenoxybenzyl (±)-cis,trans-3-(2,2-dichlorovinyl)-2,2-dimethylcyclopropanecarboxylate.

The proportions of (A) to (B) can vary over a wide range. Usually 1-100 parts of (A) and 1-100 parts of (B) are employed. Parts, proportions and percentages in this specification are by weight unless otherwise indicated. Preferably, the proportions of (A) to (B) are from 1:10 to 10:1.

In a particular embodiment, (B) comprises a synthetic pyrethroid e.g. fenvalerate and the proportions of bendiocarb to synthetic pyrethroid are 1-10:1 respectively. In another particular embodiment, (B) comprises methyl parathion and the proportions of bendiocarb to methyl parathion are 0.1-1:1 respectively.

The present combination of (A) and (B) is usually employed in the form of a composition comprising (A) and (B). The composition may be formulated as a concentrate which is diluted, generally with water, for application. A concentrate may contain for instance 5-90% in toto of (A) and (B). The composition applied to the locus to be treated may contain for instance 0.001 to 5% in toto of (A) and (B). Thus, usually the present compositions contain 0.001 to 90% in toto of (A) and (B).

The compositions comprising (A) and (B) usually contain at least one material selected from surface active agents, carriers, stickers, fertilizers, other synergists and other pesticides, particularly a surface active agent and/or a carrier.

The carrier may be a liquid, e.g. water (e.g. water used to dilute a concentrate for application). An organic solvent may be present with the water. This organic solvent may be for example a water-immiscible solvent, for instance a hydrocarbon which boils within the range 130°-270° C., in which (B) was dissolved or suspended before admixing with the water.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be a modified natural material.

Wettable powders soluble or dispersible in water may be formed by admixing the essential components with or without a carrier with a surface active agent.

The present combination may be applied to the locus to be treated in the form of a solid, e.g. dusts or granules, or, preferably, a liquid e.g. an emulsifiable concentrate of (B) and a wettable powder of (A) both dispersed in water.

An aerosol composition may be formed by admixing the essential components with a propellant, e.g. a polyhalogenated alkane such as dichlorodifluoromethane, and suitably also with a solvent.

The term 'surface active agent' is used in the broad sense to include materials variously called emulsifying agents, dispersing agents and wetting agents. Such agents are well known in the pesticide art.

The surface active agents used may comprise anionic surface active agents, for example soaps, fatty sulphate esters such as dodecyl sodium sulphate, octadecyl sodium sulphate and cetyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic agents, for example condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide.

The surface active agents may also comprise cationic agents, for example cetyl trimethylammonium bromide.

Preferred surface active agents include fatty alkyl sulphates, alkyl aryl sulphonates, fatty alkyl ethoxylates, sulphated fatty alkyl ethoxylates, dialkyl sulphosuccinate esters, the amide condensation product of oleic acid and N-methyl taurine, lignin sulphonate salts, sulphonated naphthalene-formaldehyde condensates and sulphonated urea-formaldeyde condensates.

The composition may contain a sticker, e.g. a cellulose ether, and this can prolong the residual activity by forming a coating, thus inhibiting the physical removal of active ingredient e.g. by wind, rain or rubbing.

The composition may contain a fertilizer.

(A) Bendiocarb is preferably employed as a wettable powder. When (B) is a synthetic pyrethroid e.g. fenvalerate, it is preferably employed as an emulsifiable concentrate. When (B) is methyl parathion, it is preferably employed as an emulsifiable concentrate or wettable powder.

An emulsifiable concentrate is a solution of active ingredient and surface active agent in an organic solvent. The organic solvent may be for example a water-immiscible solvent, for instance a hydrocarbon which boils within the range 130°-270° C.

A preferred embodiment is a concentrate which is a powder comprising a surface active agent, (A) bendiocarb and (B) methyl parathion.

Preferably a mixture of (A) and (B) is applied. Instead of applying (A) and (B) together to a locus, however, they may be applied in sequence with one another, e.g. separated by 1-3 days, e.g. in the form of compositions such as are discussed above containing just (A) or (B), particularly to crops within the same crop season.

(A) and (B) may be mixed, e.g. in a spray tank, immediately before use. Desirably, however, they would already have been mixed.

The invention provides a one pack presentation, in which (A) and (B) are already mixed, and also a single package designed to hold (A) and (B), e.g. in the form of compositions such as are discussed above containing just (A) or (B), in separate containers, for conjoint use, e.g. by mixing of (A) and (B), e.g. in a spray tank, for application.

The present combination of (A) and (B) may be used in sequence or admixture, particularly admixture, with another pesticide, e.g. an insecticide, acaricide or fungicide. The other pesticide is especially an insecticide or acaricide, e.g. carbofuran, carbaryl or propoxur. The other pesticide may be employed for example in such amount that the proportion of (A) to it is from 1:50 to 20:1, e.g. from 1:20 to 10:1.

When (B) comprises a synthetic pyrethroid, it may be employed with, preferably in admixture with, an additional material which is a synergist for the synthetic pyrethroid. Such an additional material may be for example piperonyl butoxide (5-(2-(2-butoxyethoxy)-ethoxymethyl)-6-propyl-1,3-benzodioxole), piprotal(-piperonal-bis(2-(2-butoxyethoxy)-ethyl acetal), sesamin (2,6-bis-(3,4-methylenedioxyphenyl)-3,7-dioxabicyclo(3,3,0)-octane) or sesamex (2-(3,4-methylenedioxyphenoxy)ethyl-3,6,9-trioxaundecane). The effect of such additional material varies with the particular synthetic pyrethroid. The amount of such additional material may be for example 2-20 parts per part of synthetic pyrethroid.

The present combination of (A) and (B) enables insects to be combated at the egg stage before they reach the damaging later stages. Preferably, application is made to the locus to be treated before substantial infestation with Insecta larvae occurs. For instance, on cotton plants one may apply against Insecta eggs for instance 7-14, preferably 7-10, days before one would first apply against the later Insecta stages. In a particular embodiment, one applies to the plants 10-14 days before one would first apply against the later Insecta stages.

The combination is active against the eggs of a wide range of Insecta, especially Insecta of the order Lepidoptera, Coleoptera or Diptera e.g. European corn borer (*Ostrinia nubilalus*), Heliothis species (e.g. *H virescens, H zea* or *H armigera*), *Alabama argillacea*, the small white butterfly (*Pieris rapae*), the Mediterranean fruit fly (*Ceratitis capitata*), the diamond-backed moth (*Plutella maculipennis*), the green rice leafhopper (*Nephotettix spp* e.g. *N cincticeps*) and the rice stem borer (*Chilo suppresalis*). Of particular interest is use against insecta of the order Lepidoptera or Diptera, especially Lepidoptera.

The combination may be applied for instance to plants, the land, soil, aquatic areas, animals or materials (e.g. stored products). Preferably the combination is applied to a locus at which a crop is growing or less preferably is to grow. The crop may be for instance a food crop e.g. maize (*Zea mays*), rice (*Oryza spp*), soybeans (*Glycine spp*) or fruit (especially tree fruit such as apples or citrus fruit) or a plantation or forestry crop e.g. conifers, cotton (*Gossypium spp*) or tobacco (*Nicotiana tabacum*). Preferably the crop is cotton, tobacco, maize or rice.

In a preferred embodiment, Insecta eggs are combated on cotton plants by applying the combination to the plants.

In another preferred embodiment, Insecta eggs are combated on maize plants by spraying onto the plants a liquid Insecta egg combating composition comprising the combination.

The combination may be applied once or more than once. Thus, for some crops, e.g. cotton, one may apply the combination periodically, e.g. 5-15 times, through the Insecta season.

In the Insecta season, the combination is usually applied, or first applied, to cotton plants before the count of Insecta eggs reaches 3 per plant. Preferably, it is applied, or first applied, when the Insecta egg count first reaches ¼ per plant, and especially as soon as the eggs appear.

Generally the combination is applied at a rate in toto of (A) and (B) of 0.1-4, e.g. 0.2-1.5, kg per hectare.

When (B) is at least one of:
(a) α-cyano-3-phenoxybenzyl 3-(2,2-dibromovinyl)-2,2-dimethylcyclopropanecarboxylate,
(b) α-cyano-3-phenoxybenzyl 3-(2,2-chlorovinyl)-2,2-dimethylcyclopropanecarboxylate,
(c) 3-phenoxybenzyl 3-(2,2-dichlorovinyl)-2,2-dimethylcyclopropanecarboxylate,
(d) 5-benzyl-3-furylmethyl 3-(2,2-dichlorovinyl)-2,2-dimethylcyclopropanecarboxylate,
(e) α-cyano-3-phenoxybenzyl 2-(4-chlorophenyl)-3-methylbutyrate, and
(f) methyl parathion, the present method and composition may then be employed for combating pests in general, but especially Insecta eggs, and the discussion above applies to pests in general. The present combination when (B) is at least one of (a), (b), (c), (d), (e) and (f) is active against a wide range of pests.

Accordingly, the invention also provides a method of combating pests at a locus infested or liable to be infested with them, which method comprises applying to the locus:
(A) bendicarb; and (B) at least one pesticide selected from (a), (b), (c), (d), (e) and (f).

The invention also provides a pesticidal composition comprising:
(A) bendiocarb; and
(B) at least one pesticide selected from (a), (b), (c), (d), (e) and (f).

This combination is surprisingly advantageous. It has an unexpectedly good combination of high activity against pests, particularly Insecta eggs, and safety to crops. When (B) comprises (a), (b), (c) or (d), the mixture with (A) is surprisingly stable, e.g. against decomposition for instance by light.

When (B) comprises (a), (b), (c) or (d), the proportions of (A) to (B) may be for example from 1:50 to 40:1, usually from 1:10 to 10:1. Proportions from 1:5 to 5:1, e.g. from 1:2 to 2:1, a specific suitable proportion being 1:1, may especially be employed. Concentrates may contain for example 0.5–85% in toto of (A) and (B), and these may be diluted with water or a hydrocarbon at the point of use for application by spraying, generally such that the concentration in toto of (A) and (B) is 0.02–3%, e.g. 0.1–3%, preferably 0.15–2%. Alternatively, the compositions comprising (A) and (B) can be produced directly for application, e.g. in the form of dusts, granules, or aerosol compositions. Hence, aerosol packs containing such a composition under pressure can be produced. As illustrations of the concentrations which may be used in compositions applied to combat domestic insect pests: in a spray applied for residual effect on surfaces, a content of 0.002–0.5% (B) and 0.025–0.5% (A) may be employed; for aerosol application for residual effect on surfaces, a content of 0.002–0.5% (B) and 0.1–5% (A) may be employed; for aerosol application for the treatment of air spaces, a content of 0.002–0.5% (B) and 0.001–0.1% (A) may be employed. In addition to (a), (b), (c) or (d), other pyrethroids (which may be synthetic or natural) may be employed with them.

The combination of (A) and at least one of (a), (b), (c), (d), (e) and (f) may be employed against a wide range of pests. The pest animals are usually arthropods, especially insects or acarids, particularly insects. The pests may be public health pests. Preferably, however, the combination is employed against agricultural pests, particularly agricultural insect pests. In a preferred embodiment, application is to a locus at which crops (i.e. desired plants) are growing or are to grow, to protect them from attack by pests, e.g. seedling pests, soil pests, stem boring pests or plant hoppers. The crops may be for instance plantation or forestry crops e.g. conifers, cotton or tobacco, food crops, e.g. vegetables, notably potatoes, brassicas, onions or beans, cereals, notably wheat, barley oats, maize or rice, soybeans or sugar beet, or fruit, notably tree fruit such as apples or citrus fruit, and especially cotton or tobacco. Pests which may be combated include Coleoptera, Diptera, Lepidoptera or Hemiptera (Homoptera), for example bollworms (e.g. Heliothis spp and *Pectinophora gossypiella*), wireworms (e.g. Agriotes spp), pygmy beetle ( Atomaria), flea beetles (e.g. Chaetocnema spp), plant hoppers (e.g. *Nilaparvata lugens* or *Nephotettix virescens*), cabbage root fly (*Erioischia brassicae*), frit fly ( Oscinella frit), and stem borers (e.g. *Ostrinia nubilalis* or Busseola spp), springtails (e.g. Onychiurus spp), millipedes (e.g. *Blaniulus guttulatus*), symphylids (e.g. *Scutigerella immaculata*), cockroaches (e.g. Blattella and Periplaneta spp), mosquitoes (e.g. *Anopheles stephensi*) and houseflies (*Musca domestica*). Especially, the combination can be employed on cotton against bollworms (e.g. Heliothis spp and *Pectinophera gossypiella*), thrips and white fly, or on tobacco. Application in and around buildings is usually at a rate of 10–1,000 mg of (A) per square meter. Application to plants, the soil, land, aquatic areas and the like, e.g. to a locus where plants are growing or are to grow, is usually at a rate of 0.1–4, e.g. 0.2–1.0, kg of (A) per hectare.

The invention is illustrated by the following Examples.

EXAMPLES 1–4

Bendiocarb, methyl parathion and fenvalerate were sprayed individually or as mixtures, as shown in the table below, at the rates of active ingredient shown in the table below, in 3 separate field trials in USA onto areas where cotton was growing. The worms present in these trails were approximately 80% Heliothis virescens—the tobacco budworm and 20% H zea—the cotton bollworm. The bendiocarb used was a wettable powder containing 76% bendiocarb, the methyl parathion was an emulsifiable concentrate containing 45.6% methyl parathion, and the fenvalerate was an emulsifiable concentrate containing 30% fenvalerate. In the Examples where 2 active ingredients were employed, tank mixes of the 2 were used. The cotton was sown on 14th or 24th April and the chemical applications were made 9 or 10 times at intervals from 27th June up to 31st July. Counts were made at harvest of the number of bolls present in 6 meters of row (two 3 meter samples per area). The mean number of bolls is shown below, as is the number on corresponding untreated controls and the increase in the number of bolls afforded by the chemical treatments over the number of bolls on the untreated controls.

| Example | Rate, kg per ha | | | Number of bolls | Increase in No of bolls over Control |
|---|---|---|---|---|---|
| | Bendi-ocarb | Methyl Parathion | Fenval-erate | | |
| 1 | 0.56 | 1.12 | — | 1468 | 363 |
| 2 | 0.56 | — | 0.11 | 1821 | 716 |
| 3 | — | 1.12 | — | 1336 | 231 |
| 4 | — | — | 0.11 | 1618 | 513 |
| Control | — | — | — | 1105 | — |

It can be seen that the bendiocarb greatly improved the methyl parathion or fenvalerate.

EXAMPLES 5–8

Bendiocarb, methyl parathion and fenvalerate were sprayed individually or as mixtures, as shown in the table below, together with spray sticker (alkyl olefin aromatic compounds, 45%) at a rate of 1.25% of the spray mixture, at the rates of active ingredient specified in the table below, onto areas in USA where cotton was growing. The worms present in these trials were approximately 80% *Heliothis virescens*—the tobacco budworm and 20% H zea—the cotton bollworm. The bendiocarb used was a wettable powder containing 76% bendiocarb, the methyl parathion was an emulsifiable concentrate containing 45.6% methyl parathion, and the fenvalerate was an emusifiable concentrate containing 30% fenvalerate. In the Examples where 2 active ingredients were employed, tank mixes of the 2 were used. The cotton was sown on 14th April and the chemical applications were made 8 times at intervals from 30th June up to 28th July. On 4 dates from 13th July to 1st August, 25 terminals on each of 4 replicated plots were assessed for the number damaged. The total number of damaged terminals, and the percent reduction in damaged terminals compared with untreated controls is shown below.

| Ex. | Rate, kg per ha | | | Total Number of Damaged Terminals | Percent Reduction in Damaged Terminals |
|---|---|---|---|---|---|
| | Bendiocarb | Methyl Parathion | Fenvalerate | | |
| 5 | 0.28 | 1.12 | — | 102 | 53.6 |
| 6 | 0.28 | — | 0.11 | 51 | 76.8 |
| 7 | — | 1.12 | — | 135 | 38.6 |
| 8 | — | — | 0.11 | 90 | 59.1 |
| Control | — | — | — | 220 | — |

It can be seen that the bendiocarb greatly improved the methyl parathion or fenvalerate.

EXAMPLES 9-14

Bendiocarb was sprayed as a tank mix with permethrin or fenvalerate, at the rates of active ingredient shown in the table below, onto areas in USA where cotton was growing. The worms present in these trials were approximately 80% *Heliothis virescens*—the tobacco budworm and 20% *H zea*—the cotton bollworm. The bendiocarb was employed as a wettable powder containing 50% bendiocarb, the permethrin was employed as an emulsifiable concentrate containing 50% permethrin, and the fenvalerate was employed as an emulsifiable concentrate containing 30% fenvalerate. The chemical applications were started 10 weeks after sowing the cotton and were made 8 times at intervals of 5 days. Counts were made at harvest of the number of bolls present in 6 meters of row (two 3 meter samples per area). In each case, the chemical treatments increased greatly the number of bolls compared to the number on untreated controls.

| Example | Rate, kg per ha | | |
|---|---|---|---|
| | Bendiocarb | Permethrin | Fenvalerate |
| 9 | 0.5 | 0.1 | — |
| 10 | 0.5 | 0.05 | — |
| 11 | 0.25 | 0.1 | — |
| 12 | 0.5 | — | 0.1 |
| 13 | 0.5 | — | 0.05 |
| 14 | 0.25 | — | 0.1 |

EXAMPLES 15-20

Bendiocarb was sprayed as a tank mix with permethrin or fenvalerate, at the rates of active ingredient shown in the table below, onto areas in USA where tobacco was growing. The worms present in these trials were mainly *Heliothis virescens*—the tobacco budworm. The bendiocarb was employed as a wettable powder containing 50% bendiocarb, the permethrin as an emulsifiable concentrate containing 50% permethrin, and the fenvalerate as an emulsifiable concentrate containing 30% fenvalerate. The chemical applications were started on the flowering of the tobacco plants and were made 4 times at intervals of 5 days. Counts were made of the number of larvae. In each case, the chemical treatments reduced the number greatly compared to the number on untreated controls.

| Example | Rate, kg per ha | | |
|---|---|---|---|
| | Bendiocarb | Permethrin | Fenvalerate |
| 15 | 0.5 | 0.1 | — |
| 16 | 0.5 | 0.05 | — |
| 17 | 0.25 | 0.1 | — |
| 18 | 0.5 | — | 0.1 |
| 19 | 0.5 | — | 0.05 |
| 20 | 0.25 | — | 0.1 |

I claim:

1. A method of combating insects or destroying Insecta eggs comprising applying to the insects, eggs, a locus infested or liable to be infested therewith an insecticidally effective amount of
   (A) bendiocarb; and
   (B) methyl parathion; the proportions of (A) to (B) being from 1:10 to 1:1 by weight.
2. A method according to claim 1 wherein a mixture of (A) and (B) is applied.
3. A method according to claim 1 wherein (A) and (B) are applied to a locus at which a crop is growing.
4. A method according to claim 1 wherein the crop is cotton.
5. A method according to claim 1 wherein (A) and (B) are applied to a locus at which cotton is growing.
6. An Insecta ovicidal composition comprising
   (A) bendiocarb; and
   (B) methyl parathion; the proportions of (A) to (B) being from 1:10 to 1:1 by weight.
7. A pesticidal composition comprising
   (A) bendiocarb; and
   (B) methyl parathion; the proportions of (A) to (B) being from 1:10 to 1:1 by weight.

* * * * *